United States Patent [19]

Schaffner

[11] Patent Number: 4,639,420

[45] Date of Patent: Jan. 27, 1987

[54] METHOD FOR THE IMMUNOANALYSIS OF CHOLESTEROL EPOXIDES

[76] Inventor: Carl P. Schaffner, 10 Youngs Rd., Trenton, N.J. 08619

[21] Appl. No.: 673,768

[22] Filed: Nov. 21, 1984

[51] Int. Cl.$^4$ ............... G01N 33/53; G01N 33/566; G01N 33/531; C12Q 1/60

[52] U.S. Cl. ............................... 435/7; 435/11; 435/15; 436/501; 436/543; 436/817; 436/822; 436/823

[58] Field of Search ............... 935/110; 435/7, 11, 435/15; 436/501, 543, 545, 546, 547, 548, 800, 817, 822, 804, 823

[56] References Cited

FOREIGN PATENT DOCUMENTS 5088219 11/1973 Japan .
4058490 10/1977 Japan .
WO84/817 12/1984 PCT Int'l Appl. .

OTHER PUBLICATIONS

Harris et al, 'Enzymes Immunoassays', Methods in Cancer Research, vol. 20, ed. by H. Bush & L. C. Yeoman, 1982.
Sparer et al, Urology, vol. 20, No. 3, 1982, pp. 244–250.
O'Neil et al, J. of Immunology, vol. 116, No. 2, 1976, pp. 363–366.
Forest et al, Steroids, vol. 28, No. 6, 1976, pp. 815–827.

Primary Examiner—Christine M. Nucker
Assistant Examiner—Patricia L. DeSantis
Attorney, Agent, or Firm—Flehr, Hohbach, Test, Albritton & Herbert

[57] ABSTRACT

An immunoassay is provided for cholesterol epoxide. To prepare the antibodies used in the immunoassay, novel immunogens, are prepared which comprise a 3,5(6)-transdiaxial-dihydroxycholestane-6(5)-yl-hapten adduct linked to a covalently bonded bridge to a carrier protein. To detect cholesterol epoxide in the sample, it is converted to the hapten adduct, then contacted with the selected antibody.

9 Claims, No Drawings

METHOD FOR THE IMMUNOANALYSIS OF CHOLESTEROL EPOXIDES

This invention is directed to a specific and precise method for the qualitative and quantitative analysis of cholesterol epoxides in biological products, secretions, fluids and tissues by employing a combination of enzymatic or chemical and immunological procedures.

BACKGROUND OF THE INVENTION

The present invention relates in part with the observations that the cholesterol epoxides are found in animal products arising either metabolically or by autoxidation. In the presence of molecular oxygen and light cholesterol readily autoxidizes to form predominantly cholesterol $5\beta,6\beta$-epoxide and a minor proportion of the isomeric, cholesterol $5\beta,6\beta$-epoxide. The degree of autoxidation increases with time and temperature. The cholesterol epoxides, thus, are found in aged cholesterol-rich products, such as dried egg products.

Of major importance, however, are the cholesterol epoxides which form metabolically in a variety of organs and tissues, such as the liver, male prostate gland, and female breast. As highly transient metabolic intermediates in the pathway from cholesterol to cholestane $3\beta,5\alpha,6\beta$-triol, a suspected regulator of endogenous cholesterol synthesis, the cholesterol epoxides normally never accumulate nor are they generally detectable with analytical procedures currently available to clinical scientists.

However, associated with various pre-developmental or existing pathological states, the cholesterol epoxides do accumulate in the related tissues and secretions. Initially, as a dose-dependent response cholesterol $5\alpha,6\alpha$-epoxide was detected in the skin of humans and animals after exposure to ultraviolet irradiation. Likewise the cholesterol epoxides are present in the serum of patients suffering with familial hypercholesterolemia where the serum cholesterol levels are also elevated. Tissue epoxycholesterol accumulation has also been seen in the rare but fatal Wolman's disease.

Of major importance is the more recent observation that the cholesterol epoxides are found in the tissues and secretions of the aging human prostate gland. This observation is particularly consistent with the development of benign and malignant diseases. The epoxycholesterols have also been observed with aging in female breast secretions and are associated with the high risk category for development of breast cancer. The female breast and male prostate are both hormone-regulated glandular secretory organs producing significant quantities of cholesterol. Significant increases of the cholesterol content of serum, prostate tissues and breast aspirates are now associated with the appearance of the epoxycholesterols, suggesting some loss of regulation of cholesterol synthesis and metabolism.

The possible role of cholesterol and its metabolites in mutagenesis and carcinogenesis has long been a controversial subject. The earliest observation revealed the production of sarcomas and other tumors when cholesterol epoxides were administered subcutaneously to experimental animals. The formation of tumors after ultraviolet irradiation of skin has been correlated with the initial formation of cholesterol $5\alpha,6\alpha$-epoxide. Likewise, cholesterol epoxides, due to the angiotoxicity of oxygenated sterols and not cholesterol itself, are suspect in the development of arterial wall damage leading to the eventual emergence of atherosclerotic lesions and cardiovascular blockage.

There is sufficient evidence that the cholesterol epoxides produce a similar degree of chromosome damage and DNA repair synthesis as low doses of ultraviolet irradiation. Cholesterol $5\alpha,6\alpha$-epoxide forms a strong physical bond with DNA leading to significant covalent attachment of the steroid to this macromolecule. Likewise, it has been demonstrated with hamster embryonic cells that cholesterol $5\alpha,6\alpha$-epoxide is as potent a carcinogen as the well recognized 3-methylcholanthrene. This cholesterol metabolite has also been implicated as an etiologic agent in human colon cancer.

In considering that many well known exogenous carcinogens undergo metabolic activation to the electrophilic "ultimate carcinogen" by endogeneous metabolic epoxidation reactions, it would be expected that the electrophilic cholesterol epoxides may also play an important role in a wide variety of cytotoxic, mutagenic and carcinogenic physiological reactions. Their detection and quantitation in biological fluids and tissues has become of increasing importance in clinical medicine.

The consistent presence of the epoxycholesterols in prostatic secretions may be diagnostic for the development of both benign and malignant diseases of the human and canine prostate gland. Likewise, detection of the cholesterol epoxides in female breast aspirates may be associated as a risk factor for the development of benign breast disease and breast cancer. Since the cholesterol epoxides are detected in the serum of patients suffering with familial hypercholesterolemia which normally results in early death due to advanced atherosclerosis, the appearance of these cholesterol metabolites in serum may serve as an important risk factor for the development of coronary vascular disease.

The qualitative and quantitative measurement of the cholesterol epoxides in biological fluids and tissues due to their relatively low concentration has been a difficult, costly and time-consuming task. The procedures of thin layer chromatography, high performance liquid chromatography, gas-liquid chromatography, nuclear magnetic resonance spectrometry, and mass spectrometry have all been employed either alone or in combination for the detection, characterization and quantitative measurement of the cholesterol epoxides in different biological fluids and tissues. While important in research projects as experimental procedures, these do not lend themselves readily to routine, quick, precise and economical clinical analyses in medical practice.

A usual procedure for the development of the immunoassay for cholesterol epoxides might follow a series of well-established methods. Normally, cholesterol epoxide, itself not antigenic as a "hapten", would be complexed through stable covalent bonds to a normally antigenic molecule such as a protein. Protein "carriers", such as bovine serum albumin, ovalbumin and bovine gamma globulin are often employed for this purpose. The cholesterol epoxide-protein complex or "immunogen" would then be introduced to the blood of some living experimental animal such as the mouse, rat or rabbit. With the recognition of the presence of a foreign antigenic substance, the animal in turn would then consequently produce a specific protein called "antibody" which has the specific ability to complex with the foreign cholesterol epoxide-containing protein or with cholesterol epoxide itself. The production of this specific antibody by the animal is the essential step in the development of an immunoassay test procedure for cholesterol epoxide. The isolation of this specific antibody protein from the blood of the animal would enable the preparation of one essential component or reagent of the immunoassay test procedure.

The reaction of the cholesterol epoxide specific antibody protein with the test product whether in serum or in breast or prostatic secretions would result in the formation of complexes that can be isolated. If the test product, cholesterol epoxide, is labelled with some enzyme or radioactive element, the amount of the label in the resultant complex then depends on the amount of product that was added for a fixed amount of standardized reagent antibody. If one combines labelled test product, as a known reference, with an unknown sample from a test patient, the product in the test sample will compete with the labelled reference product in reacting with the antibody. This will result in a decrease in the amount of label combined with the antibody. This decrease usually provides a sensitive and precise measure of the product, cholesterol epoxide, in the test sample of the patient. Thus, the cholesterol epoxide specific antibody protein and the enzyme—or radioactive—labelled cholesterol epoxide test product are the essential components of an enzyme-immuno or radioimmuno assay test procedure, respectively.

Immunoassay test procedures whether based on enzyme or radioactive element-linked antibody assays are ordinarily extremely sensitive, highly specific, and rapid by nature. While such procedures are not usually employed for the quantitation of cholesterol, itself, they are currently widely employed for the clinical analysis of other cholesterol-derived molecules, such as the steroid hormones, testosterone, 5α-dehydrotestosterone, estradiol, estrone, estriol-17β, cortisol and cortisone which like the cholesterol epoxides are normally only present in small quantities in biological fluid and tissues.

However, there is a complication encountered in the immunoassay of particular steroid hormones in that there is usually cross-reactivity of other steroids of related or similar molecular structure. As an example, antiserum for estradiol-17β could exhibit percentage cross-reaction of 94, 61, and 19 for estrone, estradiol-17α, and estriol-17β, respectively. In considering the concentration of the cholesterol epoxides in biological fluids such as serum and breast or prostatic secretions, one always finds a most significant excess of cholesterol as well. As much as a 40–100 fold greater concentration of cholesterol is usually found as compared to that of the cholesterol epoxides. Thus, with the preparation of antibodies directed towards the intact cholesterol epoxide-protein immunogen, it would be expected that cholesterol itself would exhibit some cross-reactivity with this antibody. This would reduce the usefulness of the immunoassay procedure for the cholesterol epoxides by virtue of the possibility that cholesterol itself would react, leading to false positive results.

It is therefore an object of the present invention to provide a clinical diagnostic method for the qualitative and quantitative measurement of the cholesterol epoxides based on immunological or immunoassay procedures.

SUMMARY OF THE INVENTION

The present invention provides a clinical diagnostic method for qualitatively and quantitatively measuring the presence of cholersterol epoxide. The method of preparation of the materials used in the diagnostic method utilizes a specific cholesterol epoxide reaction to produce a novel cholesterol epoxide adduct molecule, structurally highly different from that of cholesterol, cholesterol epoxide, and other related steroid molecules normally present in biological fluids and tissues. In a preferred embodiment, the enzyme, S-glutathione transferase, of the mammalian liver soluble supernatant fraction is employed to convert cholesterol 5α,6α-epoxide to the S-glutathione conjugate, 3β,5α-dihydroxycholestan-6β-yl-S-glutathione. This conjugate as a hapten is linked through stable covalent bonding to a protein carrier, such as bovine serum albumin, to produce an immunogen suitable to initiate an immune response. The resultant antibodies are sensitive and specific to the cholesterol epoxide-glutathione adduct product rather than to cholesterol epoxide itself. One or more of these antibodies may be selected for use in an immunoassay for the adduct.

The resultant antibodies, either polyclonal or monoclonal, are thus used to provide a method for determining the presence or concentration of cholesteryl epoxide in a sample of fluid. The sample will first be contacted with a hapten (preferably glutathione) in the presence of a hapten-linking agent (preferably, S-glutathione transferase) to form a ring-opened 3,5(6)-trans-diaxialdihydroxycholestane-6(5)-yl-hapten adduct. The adduct may be detected or assayed by immunoassay procedures using the prepared antibodies.

DESCRIPTION OF THE INVENTION

Glutathione (γ-glutamyl-cysteinyl-glycine) as a thiol-nucleophile is the primary substrate of S-glutathione transferase activity. This tripeptide metabolite is normally found in virtually all cells. It is an unusual tripeptide since the N-terminal glutamate is attached to cysteine via a non-α-peptidyl bond. Normally glutathione performs a wide range of metabolic functions, generally "protective" by nature. Involved in detoxification reactions it protects living cells from oxidative and free radical interactions. The initial step in the detoxification pathway involves reaction of the foreign toxic compound with the SH-group of glutathione to form an S-substituted glutathione derivative. Although these reactions proceed enzymatically with the S-glutathione transferases, some can also proceed chemically without enzyme.

As a normal detoxification reaction of the liver the interaction of cholesterol 5α,6α-epoxide with glutathione is mediated by rather specific soluble S-glutathione transferases, identified in the rat liver as two forms of S-glutathione transferase B. Generally, the S-glutathione transferases are fairly nonspecific group of soluble enzymes. In this connection, however, they appear to possess rather broad and overlapping substrate specificities. With cholesterol 5α,6α-epoxide as an electrophilic substrate, primarily only S-glutathione transferase B fractions exhibit enzymatic activity. These rather specific enzymes, as cytosol-soluble, basic liver proteins, constitute a significant portion of the soluble protein fraction of the liver. With a molecular weight of approximately 45,000 glutathione S-transferase B consists of two protein subunits of approximately equal molecular weight.

Aside from glutathione and cholesterol epoxide as substrates the enzymatic reaction with S-glutathione transferases does not require the initial formation of high energy intermediates where the participation of ATP in the reaction is necessary. The specificity of S-glutathione transferase B for cholesterol 5α,6α-epoxide is rather unique.

Pure cholesterol epoxides are not generally available from commercial sources, so they were synthesized from cholesterol. Analytical grade cholesterol, purified through the dibromide, was employed in these syntheses. Cholesterol 5α,6α-epoxide was synthesized by the procedure of Fieser, L. F. and Fieser, M., in "Reagents for Organic Synthesis," Vol. 1, 1967 John Wiley, New York, p. 136. Cholesterol (50 mmol) in methylene chloride (75 ml) solution was treated at 25° C. over a 30 minute interval with m-chloroperbenzoic acid (54 mmol) in methylene chloride (120 ml) solution. Excess peracid was destroyed by the addition of 10% sodium sulfite. Extraction of the organic layer with 5% aqueous sodium bicarbonate, water, and finally with saturated aqueous sodium chloride, followed by drying and evaporation produced a crude product readily purified by recrystallization from 88% aqueous acetone or by silica gel chromatography. Cholesterol 5α,6α-epoxide (>95% purity, m.p. 142°–143°) was obtained in >90% yield.

Cholesterol 5β,6β-epoxide was synthesized from cholesterol by the procedure of Tohma, M., Tomita, T., and Kimura, M., *Tetrahedron Letters* 44, 4359–4362 (1973). As described, 30% hydrogen peroxide (5.5 ml.) was added dropwise to a solution of cholesterol (100 mg) and ferric acetylacetonate (930 mg) in acetonitrile (100 ml) with stirring at 40° C. Excess hydrogen peroxide was destroyed with saturated aqueous sodium sulfite, and the organic phase was extracted with ethyl ether (50 ml.×3).

The combined organic layer was washed with saturated aqueous sodium chloride and dried with anhydrous sodium sulfate. The residue obtained after vacuum evaporation was purified by liquid chromatography on silica gel employing gradient elution with benzene acetone. Select fractions containing cholesterol 5β,6β-epoxide were pooled and evaporated. Recrystallization from aqueous acetone produced cholesterol 5β,6β-epoxide (m.p. 131°–134°) in 60% yield.

As components of radioimmune assay test procedures, radiolabelled cholesterol 5β,6β-epoxide and cholesterol 5β,6β-epoxide were also prepared from readily available radiolabeled cholesterol starting material employing the procedures outlined above. Both tritium— —and carbon—14 labelled cholesterol epoxides of high specific activity were prepared in this manner.

The capability of the immune system of an animal to respond to foreign antigens is strongly dependent on the molecular size of the antigen. Steroids such as the cholesterol epoxides with low molecular weights are unable by themselves to elicit antibody production. However, as haptens and as part of a macromolecular structure (immunogen) involving a protein carrier unit, the cholesterol epoxides and their derivatives as such can induce the immune system to produce antibodies that react in vitro with the hapten itself. Immunogens containing cholesterol 5α,6α-epoxide or cholesterol 5β,6β-epoxide as haptens enable the production of antibodies that react as well but to a lesser degree with cholesterol and other closely related molecules such as cholestane 3β,5α-diol, cholestane 3β, 6β-diol, or cholestane 3β,5α,6β-triol. The unique electrophilic reactivity of the cholesterol epoxides allows the use as haptens compounds derived solely directly from the reactive cholesterol epoxides. These derivatives have molecular structures sufficiently different from that of the cholesterol epoxides and cholesterol so as to impart specificity to the antibodies produced after immunization. The unique interaction of the cholesterol epoxides with glutathione, whether by chemical or enzymatic reactions, produces S-glutathione conjugates that serve as such selective haptens.

Other conjugates with cholesterol epoxide may be formed which are within the scope of the present invention. The cholesterol epoxides by virtue of their electrophilic character can undergo reaction with a wide variety of nucleophiles, other than S-glutathione, producing in many cases derivatives widely different from the parent compounds. Reactions with water and simple low molecular weight alcohols, however, would still result in products somewhat structurally—related to the cholesterol epoxides. Interaction of cholesterol 5α,-6α-epoxide and cholesterol 5β,6β-epoxide with water (hydrolysis) results in the formation of the identical product, cholestane 3β,5α,6β-triol. Similar transdiaxial cleavage of the cholesterol epoxides with other nucleophiles of more complex structure and higher molecular weight produces derivatives with structures more widely different from that of cholesterol and its reactive epoxides. Cholesterol 5α, 6α-epoxide reacts with benzenethiol (thiophenol) in the presence of catalytic amounts of phosphoric acid to yield via transdiaxial ring opening, 3β,5α-dihydroxycholestane 6β-S-yl-thiophenol. Cholesterol 5β,6β-epoxide produces in this reaction 3β,6β-dihydroxycholestane 5α-S-yl-thiophenol. Cholesterol 5α,6α-epoxide will also react with imidazole to form the 3β,5α-dihydroxycholestane 6β-imidazole adduct. The cholesterol epoxides can thus react with a wide variety other nucleophiles to produce by transdiaxial epoxide ring opening the corresponding steroid conjugate adduct. Many of these reactions may thus be employed to produce specific derivatives of the cholesterol epoxides which serve as haptens in the construction of immunogens useful for the preparation of antibodies with unique specificity for these derivatives.

In the present invention the cholesterol epoxidenucleophile reaction product or conjugate serves as the hapten. The preferred hapten is the glutathione reaction product with cholesterol 5α,6α-epoxide, namely, 3β,5α-dihydroxycholestane 6β-S-yl glutathione which serves as a hapten.

In accordance with the present invention, the hapten is further attached to a protein carrier by covalently bonded bridge molecules such as the hemisuccinate, o-carboxymethyl ether or similar structure involving the 3β-hydroxyl group of the A steroid ring, leaving the intact determinant (for example, glutathione) attached to the B ring unaltered. Loss of immunological specificity to the A steroid ring structure in the resultant antibody after immunization is believed to be of small consequence since many steroids like cholesterol have structural determinants in this part of the steroid molecule similar to the cholesterol epoxides. The immunological determinants pertinent to this invention for the reaction products of cholesterol 5α,6α-epoxide reside primarily in the 6β position of the B ring whereas that of the products derived from cholesterol 5β,6β-epoxide reside in the 5α position between the A and B rings.

The selection of the immunogenic protein carrier is generally not critical. The preparation of an immunoassay procedure according to the invention is exemplified below using bovine serum albumin as the carrier protein. With an assumed molecular weight approximating 70,000, bovine serum albumin contains about 61 terminal amino groups, not all of which are directly accessible due to protein folding. Aside from this rather well-defined protein, other protein carrier molecules can also be utilized, such as rabbit serum albumin, myoglobin, lysozyme hemoglobin, and so forth.

The attachment to the immunogenic protein carrier to the haptens, cholesterol 5α,6α-epoxide and cholesterol 5β,6β-epoxide or their reaction products with nucleophiles, may be attained through a hydrocarbon bridge, such as a succinyl bridge. Initially, both cholesterol 5α,6α-epoxide hemisuccinate and cholesterol 5β,6β-epoxide hemisuccinate were obtained by interaction of both epoxycholesterols with succinic anhydride in pyridine solution. An alternate method of joining the steroid derivative molecule to the protein carrier is the use of the O-carboxymethyl ether bridge. The 3β hydroxyl group of the cholesterol epoxides under certain conditions will react with ethyldiazoacetate or with ethyl bromoacetate to yield the O-carboxymethyl ether derivative as the ester. Alkaline saponification will then yield the 3β-O-carboxymethyl ether derivative of the cholesterol epoxides. This cholesterol epoxide bridge compound is more stable to alkaline hydrolysis than the hemisuccinate cholesterol epoxide derivatives. Other covalently-bonded bridges between the steroid hapten molecule and the protein carrier may also be used, such as disulfide, diol, diester, dicinide bridges, and so forth.

In a preferred preparation of the immunogen molecule, the cholesterol epoxide hemisuccinates or the corresponding 3β-O-carboxymethyl ether derivatives and their nucleophile derivatives may be chemically coupled to the terminal amino residues of the protein carrier, such as bovine serum albumin. A number of different coupling reactions may be employed. Preferably, the carbodiimide reaction is used to join the carboxyl group to the terminal amino group of the protein molecule forming a stable peptide bond. Other reactions, such as the mixed anhydride reaction, may also be employed to join the carboxyl group to the terminal amino group. Since the epoxide structure is sensitive to acidic conditions, it is desirable to carefully control the pH during chemical reactions involving the intact cholesterol epoxides.

The overall immune response to a steroid-protein conjugate is dependent on the molar ratio of steroid to protein in the immunogen. On the bovine serum albumin molecule not all of the amino groups are available for chemical substitution since several are masked by molecular folding so molar ratios of steroid to protein frequently range, between 15:1 and 30:1. Thus, there may not always be clear evidence of a direct correlation between the steroidprotein ratio and the titer, specificity, and affinity of the antisera directed towards the steroid hapten.

The final immunogen for the preparation of specific antibodies in the scope of this invention comprises the cholesterol epoxide nucleophile reaction product (hapten) covalently bonded to the protein carrier through a bridge involving the 3β hydroxyl group of the steroid molecule and the terminal amino groups of the protein. In the preparation of a preferred immunogen involving the hapten, 3β, 5α-dihydroxycholestane-6β-S-yl-glutathione, either the cholesterol 5α, 6α-epoxide-3β-O hemisuccinate or the cholesterol 5α, 6α-epoxide-3β-O-carboxymethyl ether derivative is condensed with the protein carrier, bovine serum albumin by the carbodiimide reaction. Finally, the epoxide functional groups of the protein bound material are reacted with glutathione to yield the ultimate immunogen. Direct carbodiimide condensation of the hapten itself, 3β, 5α-dihydroxycholestane 6β-S-yl-glutathione, to the protein carrier is also possible, but less preferable due to the potential reactivity of the carboxyl groups of the glutathione moiety. However, other cholesterol epoxide-nucleophile reaction products with nulceophile-derived structural determinants unreactive in the carbodiimide condensation process may be coupled directly to the protein carrier to form the final immunogen.

A summary of the construction of useful hapten and immunogen molecules necessary for the production of specific antibodies directed to the cholesterol epoxide-nucleophile reaction product as haptens may be reviewed as follows:

Preparation of Cholesterol Epoxide-Nucleophile Haptens

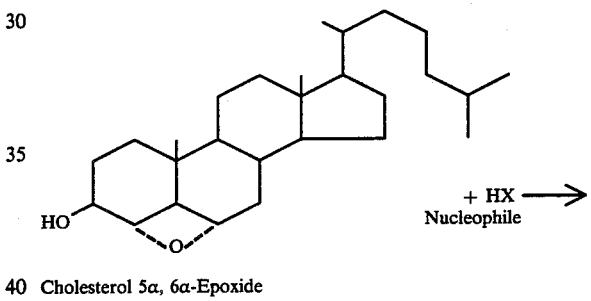

Cholesterol 5α, 6α-Epoxide

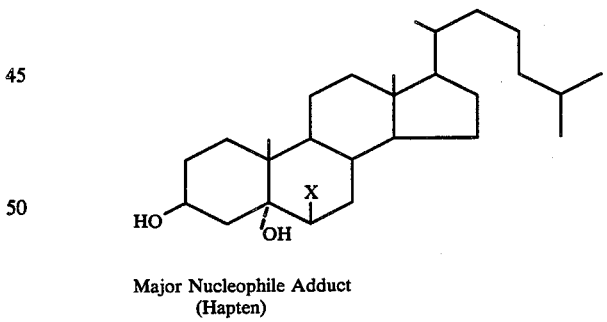

Major Nucleophile Adduct (Hapten)

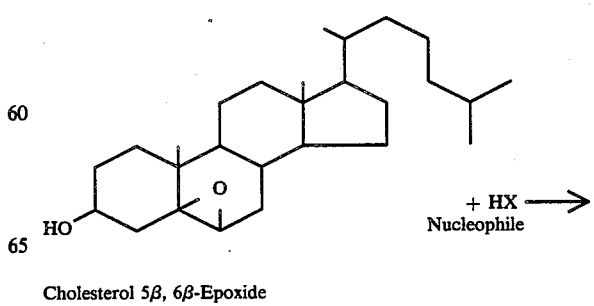

Cholesterol 5β, 6β-Epoxide

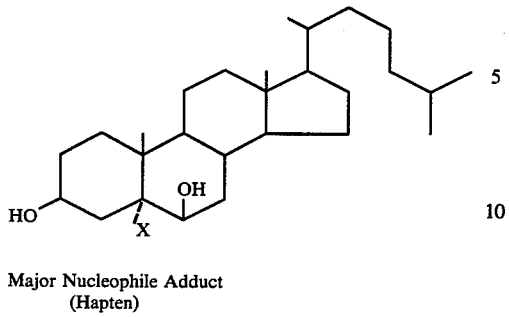

Major Nucleophile Adduct
(Hapten)

Construction of Immunogen Molecule

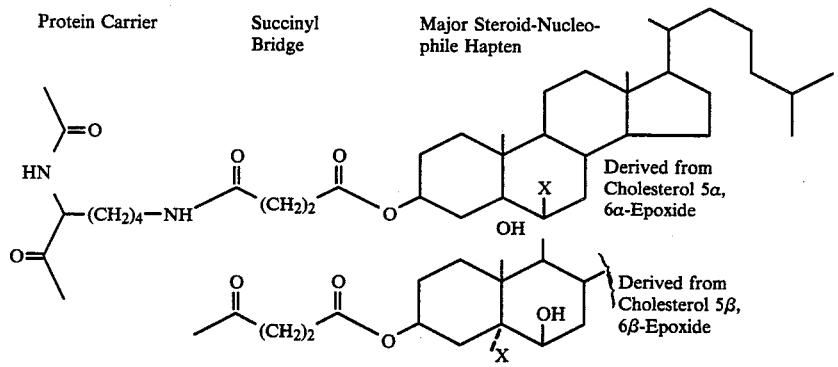

The nucleophile can be reacted with the epoxide ring of the cholesterol epoxide moiety either with the free cholesterol epoxide, its bridge derivative or with the cholesterol epoxide-containing immunogen, dependent on the nature of the nucleophile.

Cholesterol Epoxide + Nucleophile → Adduct I

Cholesterol Epoxide — Bridge + Nucleophile → Adduct II

Cholesterol Epoxide — Bridge — Protein + Nucleophile →

Adduct I is then bridged and finally coupled to protein to form the immunogen.

Adduct II is directly coupled to protein to form the immunogen.

Nucleophiles (HX)

A wide variety of nucleophilic substances can react with the electrophilic epoxides of cholesterol. Acidic conditions generally increase the electrophilic character of the epoxide. Different groups of sulfur, nitrogen, and oxygen-containing nucleophilic reagents may be cited.

Sulfur-Containing Nucleophiles-Thiols $X = -S-CH_2-CH-CO-NH-CH_2-COOH$
      $\quad\quad\quad\quad\quad |$
      $\quad\quad\quad\quad NH-CO-CH_2-CH_2-CH-COOH$
      $\quad\quad\quad\quad\quad\quad\quad\quad\quad\quad\quad\quad |$
      $\quad\quad\quad\quad\quad\quad\quad\quad\quad\quad\quad\quad NH_2$ (glutathione)

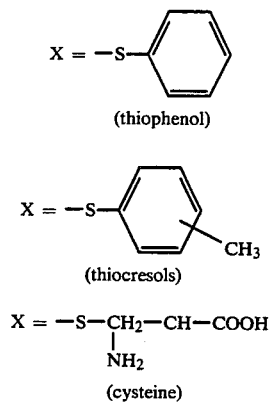

(thiophenol)

(thiocresols)

$X = -S-CH_2-CH-COOH$
      $\quad\quad\quad\quad\quad |$
      $\quad\quad\quad\quad NH_2$ (cysteine)

$X = -S-CH_2-COOH$
(thioglycolic acid)

$X = -S-CH-COOH$
      $\quad\quad |$
      $\quad CH_3$
(thiolactic acid)

$X = -S-CH-CH_2-COOH$
      $\quad\quad |$
      $\quad COOH$
(thiomalic acid)

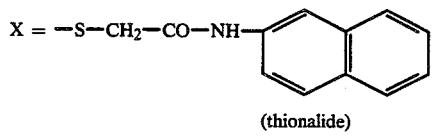
(thionalide)

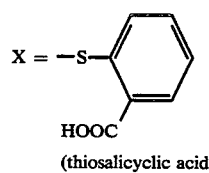
(thiosalicyclic acid)

$X = -S-CH_2CH_2-CH-COOH$
      $\quad\quad\quad\quad\quad\quad |$
      $\quad\quad\quad\quad\quad NH_2$
(homocysteine)

$X = -SR$
(alkyl thiols)

Nitrogen-Containing Nucleophiles

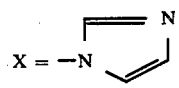
(imidazole)

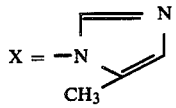
(α-methylimidazole)

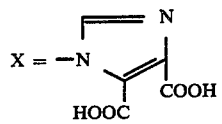
(α, β-imidazoledicarboxylic acid)

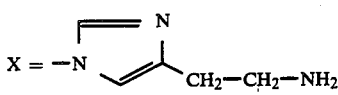
(histamine)

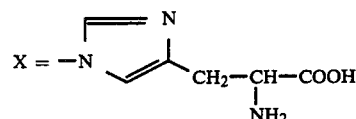
(histidine)

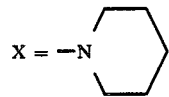
(piperidine)

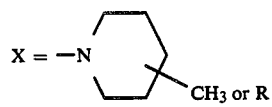
(alkyl piperidine)

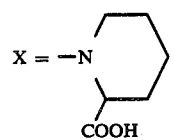
(pipecolic acid)

-continued

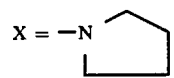
(pyrrolidine)

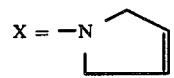
(3-pyrroline)

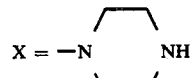
(piperazine)

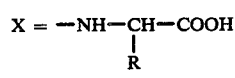
(amino acids)

Organic Acids

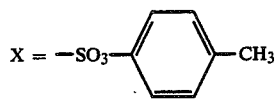
(p-toluenesulfonic acid)

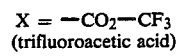
(trifluoroacetic acid)

Alcohols

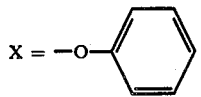
(phenol)

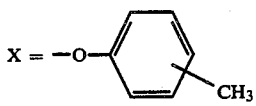
(cresols)

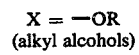
(alkyl alcohols)

Purines, Pyrimidines, Nucleosides and Nucleotides

Pyrimidine

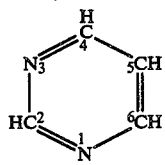

Cytosine (2-oxy-4-aminopyrimidine)

Purine

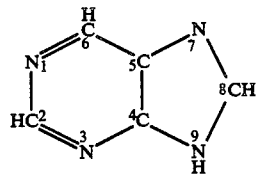

Guanine (2-amino-6-oxypurine)

Adenine (6-aminopurine)

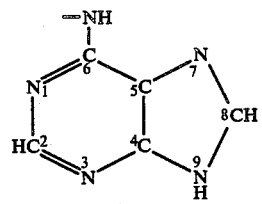

Uracil (2,4-dioxypyrimidine)

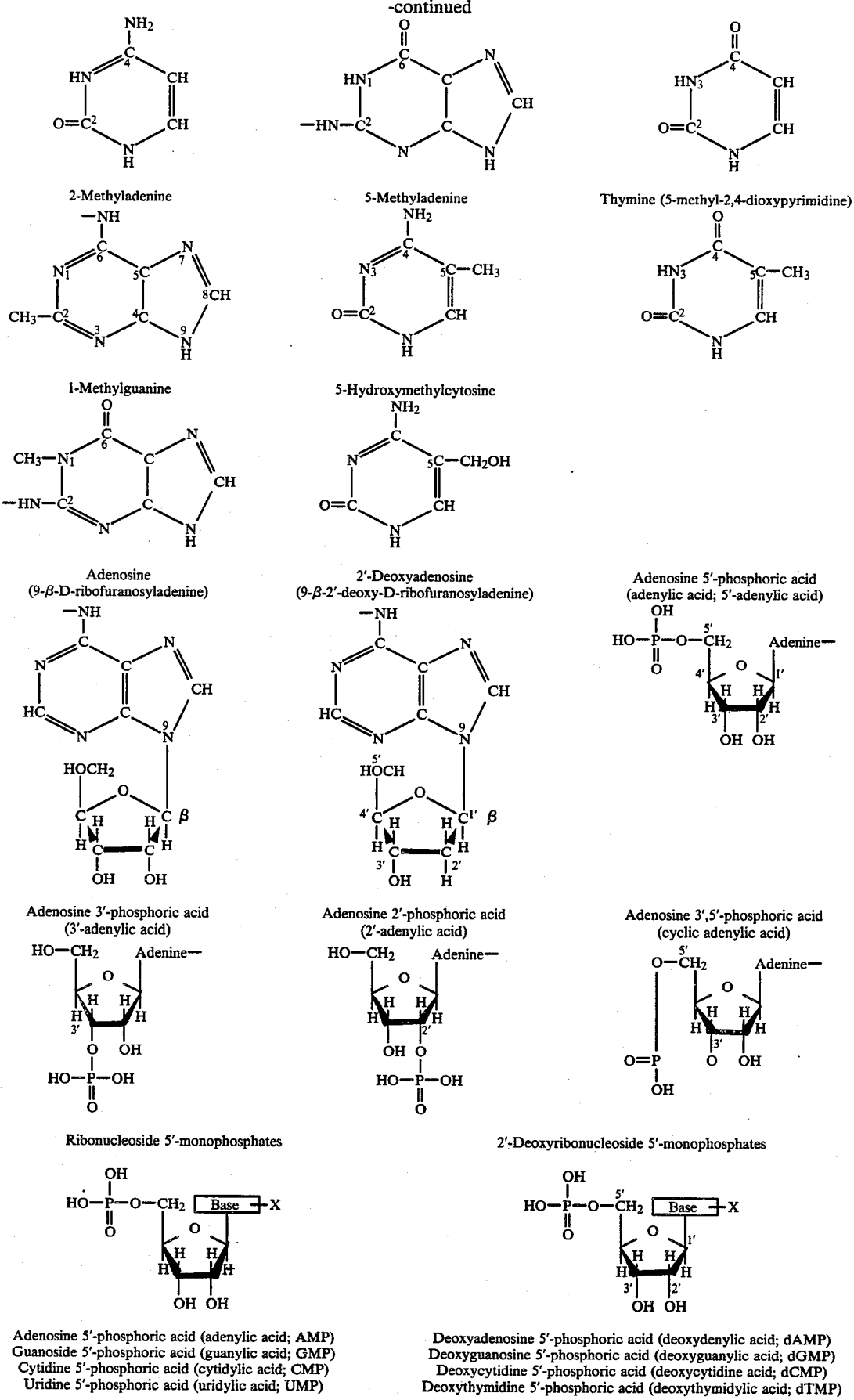

-continued

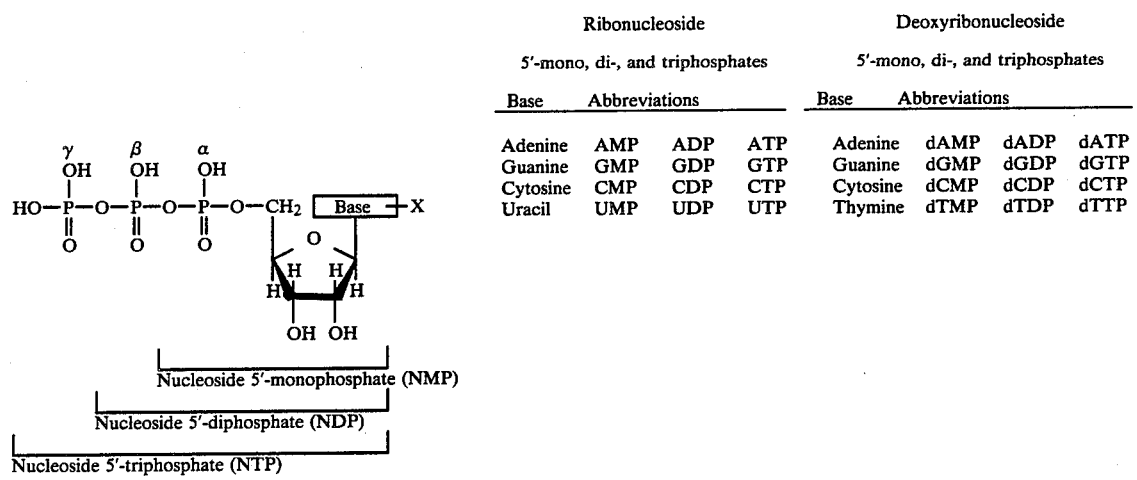

| | Ribonucleoside 5'-mono, di-, and triphosphates | | | | Deoxyribonucleoside 5'-mono, di-, and triphosphates | | |
|---|---|---|---|---|---|---|---|
| Base | Abbreviations | | | Base | Abbreviations | | |
| Adenine | AMP | ADP | ATP | Adenine | dAMP | dADP | dATP |
| Guanine | GMP | GDP | GTP | Guanine | dGMP | dGDP | dGTP |
| Cytosine | CMP | CDP | CTP | Cytosine | dCMP | dCDP | dCTP |
| Uracil | UMP | UDP | UTP | Thymine | dTMP | dTDP | dTTP |

Dinucleotide coenzymes.

Coenzyme A     Flavin adenine dinulcleotide (FAD).     Nicotinamide adenine dinucleotide (NAD).

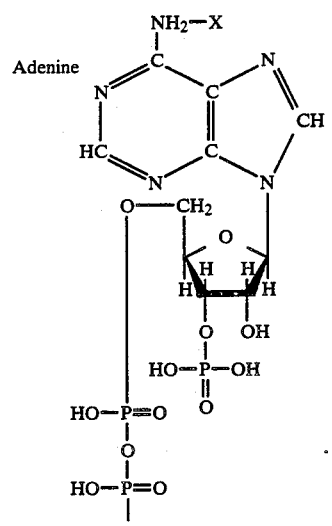 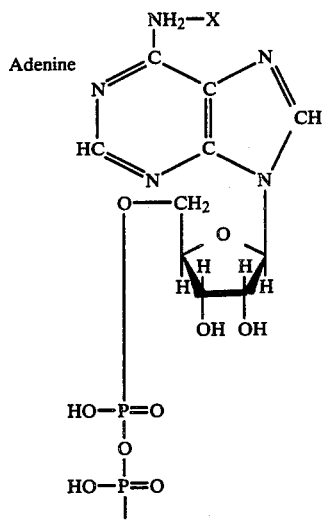 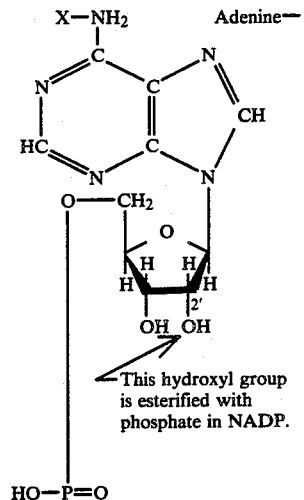

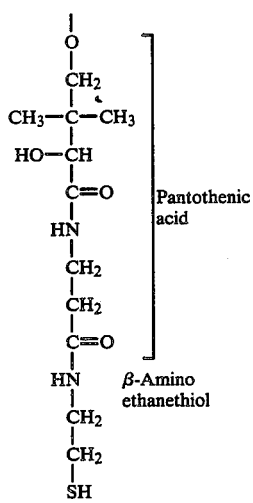 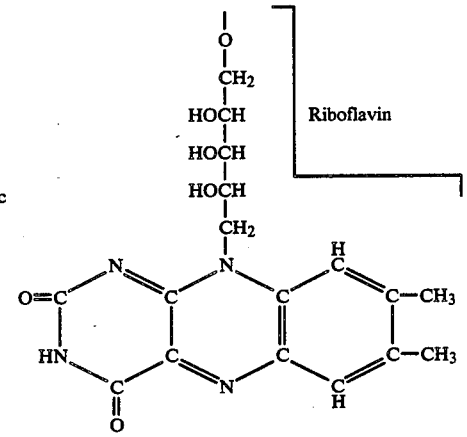 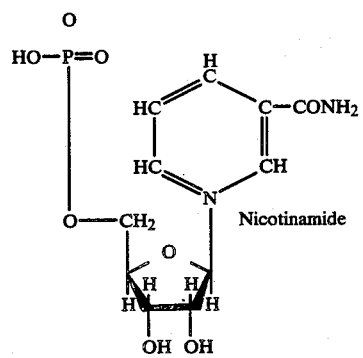

DNA            RNA

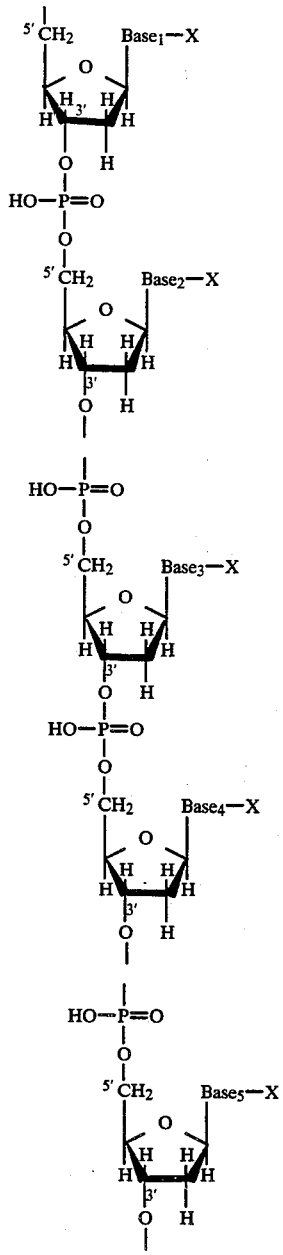
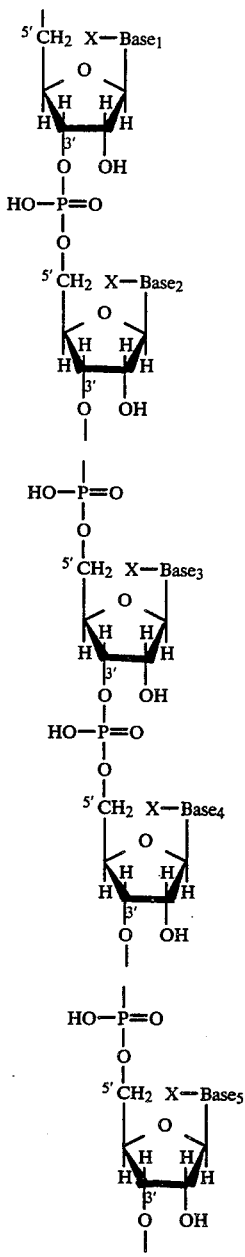

The selection of a suitable nucleophile for the interaction with the cholesterol epoxides is dependent on the reactivity of the nucleophile and the specificity of the reaction. Many nucleophiles such as the nucleic acids DNA and RNA have multiple sites of interaction. Simpler nucleophiles with a single major site of interaction with the cholesterol epoxides is preferable. In the analysis of biological specimens for cholesterol epoxide content it is also important that the conversion of any epoxide through interaction with the nucleophile be complete and readily and conveniently carried out under clinical laboratory conditions. In this regard, the interaction of the cholesterol epoxides with glutathione can be carried out under simple conditions either by enzymatic or chemical means. The resultant product is known, and as a hapten it is specifically recognized by the antibodies produced in its presence. Interaction of the cholesterol epoxides with thiophenol and imidazole also involves single specific sites. With clincial specimens these reactions can also be employed for conversion of any cholesterol epoxide present to the respective nucleophile product. Hence, the preparation of the cholesterol epoxide-nucleophile reaction product as a pure hapten and eventually coupling to an antigenic protein carrier as the final immunogen, all depend on the specificity and degree of the nucleophile-cholesterol epoxide reaction. With incomplete reactions the desirable immunogen may be obtained after purification.

After final synthesis of the immunogen, it will be purified and characterized. The steroid-nucleophile protein complexes obtained by any of the above described methods may be purified by conventional techniques to be freed from any steroid nucleophile product not covalently bound. Preferably, this may be achieved by dialysis against a constant flow of distilled water or by G-25 sephadex gel filtration. After purification, the immunogen conjugates are characterized to establish the molar ratio of hapten vs. carrier. Depending on the structural nature of the nucleophile interacted with the cholesterol epoxides, a variety of different methods involving direct ultraviolet-visible spectrophotometry, radioisotopic incorporation or hydrolytic cleavage of the immunogen may all be applied to determine the hapten vs. protein ratios.

With the availability of a suitable immunogen a great variety of well established immunization procedures can be employed for the production of antibodies specific for the hapten, specifically, the cholesterol epoxide-nucleophile reaction product. The prepared immunogen in a suitable vehicle, such as saline or oily adjuvant emulsion, can be administered by multiple intradermal, subcutaneous or intramuscular administration. Antibody response is usually relatively rapid. While almost all routes of administration such as subcutaneous, intramuscular, intravenous, and into the lymph nodes or footpads are utilized in conjunction with subsequent booster injections, it is found that multiple-site intradermal immunization yields satisfactory results without booster injections of immunogen. A great variety of animal species have been employed for the immunization process, including the mouse, rat, guinea pig, rabbit, sheep, goat and horse.

The polyclonal antibodies produced by immunization of an animal with the hapten-protein immunogen can then be recovered from the serum by known techniques. During the immunization process levels of hapten specific antisera will be monitored by bleeding the animals at regular intervals. Antisera diluted with buffers are allowed to react with hapten, and upon incubation, the reaction results in the formation of antibody-hapten complexes that may be measured and isolated by known techniques.

Monoclonal antibodies specifically directed to particular cholesterol expoxide-nucleophile haptens may also be prepared. The B lymphocytes are involved in the production of specific antibodies upon immunization of an animal. In the monoclonal method one fuses or hygridizes two somatic cells, one belonging to a neoplastic myeloma cell line and the other consisting of a normal antibody-producing B lymphocyte obtained from the immunized animal. The resulting fused cell or hybridoma retains the capacity for continuous growth from the neoplastic parent and the ability to secrete antibodies to the immunizing hapten-containing immunogen from the B-lymphocyte. Derived from a single B lymphocyte the hybridoma cell line produces only one kind of antibody. Selection of the specific hybridoma cell line producing antibodies directed only to the cholesterol epoxide-nucleophile hapten may be performed by known techniques, thereby providing continuous availability of the essential component of the immunoassay test kit.

The immunoassay test procedure for the detection and measurement of cholesterol epoxides depends on the antibody-hapten reaction and, in particular, on the preparation of antibodies specific for cholesterol epoxide-nucleophile reaction products as haptens rather than for the cholesterol epoxides themselves. It is requisite for the imunoassay that any cholesterol epoxide present in biological specimens be converted by enzymatic or chemical means to the nucleophile reaction product recognizable by the antibody. The same reagents may be used for this purpose as are used to make the original hapten used for raising the antibodies.

In order to make the antigen (hapten)-antibody reaction measurable or visible, it is necessary to tag either the antigen or antibody with a molecule demonstrable through some special inherent property such as light emission (fluorescent antibody technique), enzymatic activity (enzyme immunoassay), high electron-scanning capacity (immunoferrition method), or radioactivity (radioimmune assay).

For enzyme immunoassay procedures the hapten specific antibody may be labelled by attaching an enzyme, such as horseradish peroxidase. This enzyme may be attached to the antibody protein via bifunctional reactants such as 4,4'-difluoro-3,3'-dinitro-phenylsulfone or glutaraldehyde. The enzyme conjugated antibodies can then react with the hapten and unbound antibodies are removed by washing. The hapten-antibody complex upon reaction with hydrogen peroxide in the presence of electron donors such as diamino benzidine produces measurable color reactions.

In a similar manner the hapten (antigen) may also be labelled with an enzyme. Glucose 6-phosphate dehydrogenase is a frequently used labelling enzyme. When the enzyme-labelled hapten binds to the antibody specific for the hapten, the enzyme activity is reduced. In a typical competitive immunoassay, hapten in the biological sample competes with the enzyme-labelled hapten for the antibody, thereby reducing the inactivation of the enzyme induced by the antibody. Glucose-6-phosphate dehydrogenase activity correlates with the concentration of the hapten and is measured spectrophotometrically due to the enzymic catalysis of the substrate NAD to NADH.

When using a radioimmune assay procedure the cholesterol epoxide-nucleophile conjugate hapten may be labelled with a radioactive element, such a tritium or carbon-14. Either the cholesterol epoxide or nucleophile component can be so labelled. As an example, tritium-labelled cholesterol can be converted to the cholesterol epoxides. Interaction of these with nucleophiles such as glutathione produces tritium-labelled haptens. Also, by reacting a radioactively-labelled glutathione with cholesterol epoxide, the presence of the labelled glutathione nucleophile on the steroid nucleus may also be used as a basis for detection of the epoxide. Competition of added radio-labelled hapten with that present in the test specimen for the hapten-specific antibody serves as a basis for detection and quantitation.

The following examples represent preferred embodiments of the present invention:

EXAMPLE 1

Carbon-14 Labeled Cholesterol $5\alpha,6\alpha$-Epoxide

In a 25 ml. microflask fitted with a condenser 8 mg. (1 mCi, 20 $\mu$mol) of 4-$^{14}$C-cholesterol (50 mCi/mmol) is dissolved in methylene chloride (5 ml). Treatment at 25° C. for 30 minutes with m-chloroperbenzoic acid (25 $\mu$mol) in methylene chloride (10 ml) solution is followed by the dropwise addition of 10% aqueous sodium sulfite until a test with starch-iodide paper is negative for residual peracid. The reaction mixture transferred to a micro-separatory funnel is then washed with 5% aqueous sodium bicarbonate solution to remove the m-chlorobenzoic acid followed by aqueous saline washes. After evaporation of the solvent, the residue is crystallized from 88% aqueous acetone to give the desired 4-$^{14}$C-cholesterol 5α,6αepoxide (7 mg., 50 mCi/mmol). The radiolabeled product is diluted with unlabeled cholesterol 5α,6α-epoxide to desired specific radioactivity.

EXAMPLE 2

Tritium Labeled Cholesterol 5α,6α-Epoxide

Following the procedures of Example 1, 5 mg. (1 Ci, 13 μmol) of 1,2,6,7-$^{3}$H-cholesterol (75 Ci/mmol) is treated with m-chloroperbenzoic (15 μmol) in methylene chloride solution. The product is then recovered to yield 1,2,6,7-$^{3}$H-cholesterol 5α,6α-epoxide (4.5 mg, 75 Ci/mmol).

EXAMPLE 3

Carbon-14 Labeled Cholesterol 5β,6β-Epoxide

In a 25 ml. microflask fitted with a condenser 8 mg. (1 mCi, 20 μmol) of 4-$^{14}$C-cholesterol (50 mCi/mmol) and 75 mg ferric acetylacetonate in acetonitrile (10 ml) is treated dropwise with 30% hydrogen peroxide (0.5 ml) at 40° C. with stirring. Excessive oxidant is destroyed with saturated aqueous sodium sulfite followed by extraction with ethyl ether (5 ml.×3). Washing of the organic phase with saturated aqueous saline followed by drying with anhydrous sodium sulfate and vacuum evaporation of the solvent produces an amorphous residue. Silica gel gradient chromatography with benzene-acetone followed by recrystallization from aqueous acetone produces 4-$^{14}$C-cholesterol 5β,6β-epoxide (4 mg., 50 mCi/mmol).

EXAMPLE 4

Tritium Labeled Cholesterol 5β,6β-Epoxide

Following the procedure of Example 3, 5 mg (1 Ci, 13 μmol) of 1,2,6,7-$^{3}$H-cholesterol (75 Ci/mmol) and 50 mg ferric acetylacetonate in acetonitrile (10 ml) is treated dropwise with 30% hydrogen peroxide (0.3 ml) at 40° C. with stirring. After chromatographic purification and recrystallization 1,2,6,7-$^{3}$H-cholesterol 5β,6β-epoxide (3 mg., 75 Ci/mmol) is obtained. The radiolabeled cholesterol epoxides are diluted with unlabeled material to the desired specific activity.

EXAMPLE 5

3β,5α-Dihydroxycholestan-6β-S-yl-Glutathione (Hapten)

To a solution of cholesterol 5α,6α-epoxide (100 mg., 0.25 mmol) in ethanol (10 ml) is added glutathione (150 mg., 0.5 mmol) in water (5 ml). After addition of 5N sodium hydroxide (0.5 ml), the mixture is refluxed for 3 hours. After cooling, acidification with glacial acetic acid, and vacuum evaporation, the residue is dissolved in 1% aqueous acetic acid (5 ml) and extracted with water saturated 1-butanol (10 ml×3). Evaporation of the solvent produces a residue which is dissolved in water (5 ml) and is purified over an Amberlite XAD-2 column (40×2 cm) processed initially with successive 10 bed volumes of ethanol, methanol, water and methanol-water (1:1, v/v) washes. After addition of the reaction product the column is washed with water, methanol-water (1:1 v/v) and eluted with methanol (5:2:5 bed volumes, respectively). Evaporation of the solvent from fractions monitored by the ninhydrin reaction and thin layer chromatography on silica gel G60 plates with the solvent system, 1-butanol-gl. acetic acid-water (4:1:5, v/v/v) produces an amorphous residue (145 mg.) exhibiting a single ninhydrin-positive component.

EXAMPLE 5A

Biotransformation of Cholesterol 5α,6α-Epoxide to 3β,5α-Dihydroxycholestan-6β-S-yl-Glutathione Cholesterol 5α,6α-epoxide (20 μg, 0.05 μmol) in human prostatic fluid (1 ml) is incubated at 37° for 30 min. with a soluble rat liver S-glutathione transferase β (10 mg.) in the presence of glutathione (6 mg., 20 μmol) in 0.1M potassium phosphate buffer, pH 7.0 to a final volume of 10 ml. The reaction product, 3β,5α-dihydroxycholestan-6β-S-yl-glutathione, is measurable either as a hapten by specific antibody reaction or by direct extraction and purification.

EXAMPLE 6

3β,6β-Dihydroxycholestan-5α-S-yl-Glutathione (Hapten)

Following the procedure of Example 5, cholesterol 5β,6β-epoxide (100 mg., 0.25 mmol) in water (5 ml) and refluxed for 3 hours after the addition of 5N sodium hydroxide (0.5 ml). Extraction of the reaction mixture followed by purification on Amberlite XAD-2 as outlined in Example 5 yields an amorphous product (130 mg.) exhibiting a single ninhydrin-positive component on silica gel G-60 thin layer chromatography with the solvent system, 1-butanol-gl. acetic acid-water (4:1:5, v/v/v).

EXAMPLE 7

3β,5α-Dihydroxycholestan-5β-S-yl-Cystein (Hapten)

Following the procedure of Example 5, cholesterol 5α,6α-epoxide (100 mg., 0.25 mmol) in ethanol (10 ml.) is added to L-cysteine (60 mg., 0.50 mmol) in water (5 ml) and refluxed for 3 hours after the addition of 5N sodium hydroxide (0.5 ml). Extraction of the reaction mixture followed by chromatographic purification on Amberlite XAD-2 yields an amorphous product (105 mg.) exhibiting a single ninhydrin-positive component on silica gel G-60 thin layer chromatography with the solvent system, 1-butanol-formic acid-water (4:1:2, v/v/v).

EXAMPLE 8

3β,6β-Dihydroxycholestan-5α-S-yl-Cysteine (Hapten)

Following the procedure of Example 5, cholesterol 5β,6β-epoxide (100 mg., 0.25 mmol) in ethanol (10 ml.) is added to L-cysteine (60 mg., 0.50 mmol) in water (5 ml) and refluxed for 3 hours after the addition of 5N sodium hydroxide (0.5 ml). Extraction of the reaction mixture followed by chromatographic purification on Amberlite XAD-2 yields an amorphous product (98 mg.) exhibiting a single ninhydrin-positive component on silica gel G-60 thin layer chromatography with the solvent system, 1-butanol-formic acid-water (4:1:2, v/v/v).

EXAMPLE 9

3β,5α-Dihydroxycholestan-6β-S-yl-Thiophenol (Hapten)

In a 50 ml flask fitted with a condenser cholesterol 5α,6α-epoxide (100 mg., 0.25 mmol) in benzene (10 ml) solution is treated dropwise with a benzene (10 ml) solution of thiophenol (55 mg., 0.5 mmol) containing a few drops of concentrated phosphoric acid. The mixture is refluxed for 1 hour. After cooling, the reaction mixture is evaporated under vacuum to an oily residue which is redissolved in ethyl ether (25 ml). The resultant solution is extracted with 5% aqueous sodium carbonate solution (10 ml.×2), dried with anhydrous sodium sulfate, and evaporated under vacuum. The resultant residue is purified by liquid chromatography on silica gel G-60 employing chloroform-methanol gradient elution. Combination of fractions containing the desired product followed by vacuum evaporation produces an amorphous substance (85 mg) exhibiting a single component by ultraviolet absorption on silica gel G-60 thin layer chromatographic plates after development with the solvent system, 1-butanol-gl. acetic acid-water (3:1:5, v/v/v).

EXAMPLE 10

3$\beta$,6$\beta$-Dihydroxycholestan-5$\alpha$-S-yl-Thiophenol (Hapten)

Following the procedure of Example 9 cholesterol 5$\beta$,6$\beta$-epoxide (100 mg., 0.25 mmol) in benzene (10 ml) solution is treated with a benzene (10 ml) solution of thiophenol (55 mg., 0.5 mmol) containing a few drops of concentrated phosphoric acid. The reaction mixture is found to contain 3$\beta$,6$\beta$-dihydroxycholestan-5$\alpha$-S-yl-thiophenol which is recovered by the procedure outlined in Example 9. The amorphous product (35 mg) exhibits a single ultraviolet-absorbing component on silica gel thin layer chromatography with the solvent system, 1-butanol-gl. acetic acid-water (3:1:5, v/v/v).

EXAMPLE 11

3$\beta$,5$\alpha$-Dihydroxycholestan-6$\beta$-S-yl-O-Thiocresol (Hapten)

Following the procedure of Example 9 cholesterol 5$\alpha$,6$\alpha$-epoxide (100 mg., 0.25 mmol) is treated with O-thiocresol (60 mg., 0.50 mmol), and the desired product, 3$\beta$,5$\beta$-dihydroxycholestan-6$\beta$-S-yl-O-thiocresol, is recovered as an amorphous solid (75 mg.)

EXAMPLE 12

3$\beta$,6$\beta$-Dihydroxycholestan-5$\alpha$-S-yl-O-Thiocresol (Hapten)

Following the procedure of Example 9 cholesterol 5$\beta$,6$\beta$-epoxide (100 mg., 0.25 mmol) is treated with O-thiocresol (60 mg., 0.50 mmol), and the desired product, 3$\beta$,6$\beta$-dihydroxycholestan-5$\alpha$-S-yl-O-thiocresol, is recovered as an amorphous solid (40 mg.)

EXAMPLE 13

3$\beta$,5$\alpha$-Dihydroxycholestan-6$\beta$-S-yl-m-Thiocresol (Hapten)

Following the procedure of Example 9 cholesterol 5$\alpha$,6$\alpha$-epoxide (100 mg., 0.25 mmol) is treated with m-thiocresol (60 mg., 0.50 mmol), and the desired product, 3$\beta$,5$\alpha$-dihydrocholestan-6$\beta$-S-yl-m-thiocresol, is recovered as an amorphous solid (72 mg.).

EXAMPLE 14

3$\beta$,6$\beta$-Dihydroxycholestan-5$\alpha$-S-yl-m-Thiocresol (Hapten)

Following the procedure of Example 9 cholesterol 6$\beta$,6$\beta$-epoxide (100 mg., 0.25 mmol) is treated with m-thiocresol (60 mg., 0.50 mmol), and the desired product, 3$\beta$,6$\beta$-dihydroxycholestan-5$\alpha$-S-yl-m-thiocresol, is recovered as an amorphous solid (30 mg.)

EXAMPLE 15

3$\beta$,5$\alpha$-Dihydroxycholestan-6$\beta$-S-yl-p-thiocresol (Hapten)

Following the procedure of Example 9 cholesterol 5$\alpha$,6$\alpha$-epoxide (100 mg., 0.25 mmol) is treated with p-thiocresol (60 mg., 0.50 mmol), and the desired product, 3$\beta$,5$\alpha$-dihydrocholestan-6$\beta$-S-yl-p-thiocresol, is recovered as an amorphous solid (80 mg.).

EXAMPLE 16

3$\beta$,6$\beta$-Dihydroxycholestan-5$\alpha$-S-yl-Thiocresol (Hapten)

Following the procedure of Example 9 cholesterol 5$\beta$,6$\beta$-epoxide (100 mg., 0.25 mmol) is treated with p-thiocresol (60 mg., 0.50 mmol), and the desired product, 3$\beta$,6$\beta$-dihydroxycholestan-5$\alpha$-S-yl-p-thiocresol, is recovered as an amorphous solid (38 mg.)

EXAMPLE 17

3$\beta$,5$\alpha$-Dihydroxycholestan-6$\beta$-S-yl-Thioglycolic Acid (Hapten)

In a 50 ml flask fitted with a condenser cholesterol 5$\alpha$,6$\alpha$-epoxide (100 mg., 0.25 mmol) in ethanol (10 ml) solution is refluxed for 2 hours with thioglycolic acid (46 mg., 0.50 mmOl) dissolved in 0.5N aqueous sodium hydroxide (5 ml). After cooling, the reaction mixture is acidified with glacial acetic acid and evaporated under vacuum. The oily residue is extracted with benzene (5 ml×3), and the combined extracts dried with anhydrous sodium sulfate. After vacuum evaporation, the residue is purified by silica gel G-60 liquid column chromatography employing chloroform-methanol gradient elution. The product, 3$\beta$,5$\alpha$-dihydroxycholestan-6$\beta$-S-yl-thioglycolic acid, is obtained as an amorphous solid (80 mg.) from evaporation of selective chromatographic fractions.

EXAMPLE 18

3$\beta$,5$\beta$-Dihydroxycholestan-5$\alpha$-S-yl-Thioglycolic Acid (Hapten)

Following the procedure of Example 17 cholesterol 5$\beta$,6$\beta$-epoxide (100 mg., 0.25 mmol) is treated with thioglycolic acid (46 mg., 0.50 mmol) in 0.5N sodium hydroxide solution (5 ml). After extraction and silica gel liquid chromatography with chloroform-methanol gradient elution, the product, 3$\beta$,6$\beta$-dihydroxycholestan-5$\alpha$-S-yl-thioglycolic acid, is obtained from selected fractions upon evaporation as an amorphous solid (33 mg.).

EXAMPLE 19

3$\beta$,5$\alpha$-Dihydroxycholestan-6$\beta$-S-yl-Thiolactic Acid (Hapten)

Following the procedure of Example 17 cholesterol 5$\alpha$,6$\alpha$-epoxide (100 mg., 0.25 mmol) is treated with thiolactic acid (53 mg., 0.50 mmol) in 0.5N sodium hydroxide solution (5 ml). Upon extraction and liquid chromatographic purification the product, 3$\beta$,5$\alpha$-dihydroxycholestan-6$\beta$-S-yl-thiolactic acid, is obtained from selected fractions upon evaporation as an amorphous solid (75 mg.)

EXAMPLE 20

3β,6β-Dihydroxycholestan-5α-S-yl-Thiolactic Acid (Hapten)

Following the procedure of Example 17 cholesterol 5β,6β-epoxide (100 mg., 0.25 mmol.) is treated with thiolactic acid (53 mg., 0.50 mmol) in 0.5N sodium hydroxide solution (5 ml). After extraction and chromatographic purification the product, 3β,6β-dihydroxycholestan-5α-S-yl-thiolactic acid, is obtained from selected fractions as an amorphous solid (30 mg.).

EXAMPLE 21

3β,5α-Dihydroxycholestan-6β-S-yl-Thiosalicyclic Acid (Hapten)

Following the procedure of Example 17 cholesterol 5α,6α-epoxide (100 mg., 0.25 mmol) is treated with thiosalicyclic acid (77 mg., 0.50 mmol) in 0.5N sodium hydroxide solution (5 ml). After extraction, chromatographic purification, and evaporation of selected fractions, the product, 3β,5α-dihydroxycholestan-6β-S-yl-thiosalicyclic acid, is obtained as a microcrystalline solid (110 mg.).

EXAMPLE 22

3β,6β-Dihydroxycholestan-5α-S-yl-Thiosalicyclic Acid (Hapten)

Following the procedures of Example 17 cholesterol 5β,6β-epoxide (100 mg., 0.25 mmol.) is treated with thiosalicyclic acid (77 mg., 0.50 mmol) in 0.5N sodium hydroxide solution (5 ml). After extraction, chromatographic purification, and evaporation of selected fractions, the product, 3β,6β-dihydroxycholestan-5α-S-yl-thiosalicyclic acid, is obtained as a semicrystalline solid (43 mg.).

EXAMPLE 23

3β,5α-Dihydroxycholestan-6β-S-yl-2-Thiouracil (Hapten)

Following the procedure of Example 17 cholesterol 5α,6α-epoxide (100 mg., 0.25 mmol) is treated with 2-thiouracil (64.mg., 0.50 mmol) in 0.5N sodium hydroxide solution (5 ml). After extraction, chromatographic purification, and evaporation of selected fractions, the product. 3β,5α-dihydroxycholestan-6β-S-yl-2-thiouracil, is obtained as a semicrystalline solid (101 mg.).

EXAMPLE 24

3β,6β-Dihydroxycholestan-5α-S-yl-2-Thiouracil (Hapten)

Following the procedure of Example 17 cholesterol 5β6β-epoxide (100 mg., 0.25 mmol) is treated with 2-thiouracil (64 mg., 0.50 mmol) in 0.5N sodium hydroxide solution (5N). After extraction, chromatographic purification, and evaporation of selected fractions, the product, 3β,6β-dihydroxycholestan-5α-S-yl-2-thiouracil, is obtained as a semicrystalline solid (38 mg).

EXAMPLE 25

3β,5α-Dihydroxycholestan-6β-O-p-Toluenesulfonate (Hapten)

In a 50 ml. flask fitted with a stirrer, cholesterol 5α,-6α-epoxide (100 mg., 0.25 mmol) in benzene (10 ml) solution is combined with p-toluenesulfonic acid (86 mg., 0.50 mmol) in benzene (10 ml) and stirred for 4 hours at room temperature. The reaction mixture is extracted with 5% aqueous sodium bicarbonate solution (5 ml×3), followed by water washes and drying with anhydrous sodium sulfate. Vacuum evaporation of the solvent produces an oily residue. Purification with silica gel G-60 liquid chromatography employing chloroform-methanol gradient elution produces selected fractions containing the product, 3β,5α-dihydroxycholestan-6β-O-p-toluenesulfonate. Upon vacuum evaporation the product is obtained as a semicrystalline solid (70 mg.).

EXAMPLE 26

3β,6β-Dihydroxycholestan-5α-O-p-Toluenesulfonate (Hapten)

Following the procedure of Example 25 cholesterol 5β-6β-epoxide and p-toluenesulfonate are combined in 1:2 molar ratio. After reaction the product, 3β,6β-dihydroxycholestan-5β-O-p-toluenesulfonate, is purified by silica gel chromatography and recovered as a semicrystalline solid.

EXAMPLE 27

3β,5α-Dihydroxycholestan-6β-O-Trifluoroacetate (Hapten)

Following the procedure of Example 25 cholesterol 5α,6α-epoxide and trifluoroacetic acid are combined in 1:2 molar ratio. After reaction the product, 3β,5α-dihydrocholestan-6β-O-trifluoroacetate, is purified by silica gel chromatography and recovered as an amorphous solid.

EXAMPLE 28

3β,6β-Dihydroxycholestan-5α-O-Trifluoroacetate (Hapten)

Following the procedure of Example 25 cholesterol 5β,6β-epoxide and trifluoroacetic acid are combined in 1:2 molar ratio. After reaction the product, 3β,6β-dihydroxycholestan-5α-O-trifluoroacetate, is purified by silica gel chromatography and recovered as an amorphous solid.

EXAMPLE 29

3β,5α-Dihydroxycholestan-6β-N-yl-Imidazole (Hapten)

In a 50 ml. flask fitted with a stirrer cholesterol 5α,-6α-epoxide (100 mg., 0.25 mmol) in ethanol (10 ml) solution is combined with imidazole (35 mg., 0.5 mmol) in ethanol (10 ml). The reaction mixture is stirred at 80° C. for 4 hours. Upon vacuum evaporation of the solvent an oil residue remains. Silica gel G-60 liquid column chromatography with chloroform-methanol gradient elution provides fractions containing the imidazole adduct product of cholesterol 5α,6α-epoxide. Upon evaporation of the solvents under vacuum an amorphous product (41 mg.) is produced.

EXAMPLE 30

3β,6β-Dihydroxycholestan-5α-N-yl-Imidazole (Hapten)

Following the procedure of Example 29 cholesterol 5β,6β-epoxide and imidazole in 1:2 molar ratio interact to form the desired product which is recovered.

EXAMPLE 31

Cholesterol 5α,6α-Epoxide-α-Methyl Imidazole Adduct (Hapten)

Following the procedure of Example 29 cholesterol 5α,6α-epoxide and α-methylimidazole in 1:2 molar ratio produce the desired product.

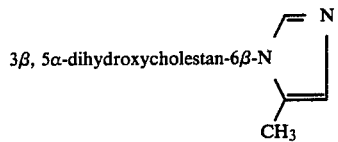

EXAMPLE 32

Cholesterol 5β,6β-Epoxide-α-Methyl Imidazole Adduct (Hapten)

Following the procedure of Example 29 cholesterol 5β,6β-epoxide and α-methyl imidazole in 1:2 molar ratio produce the desired product.

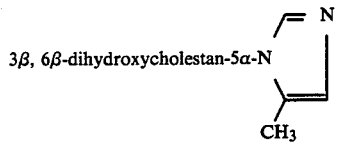

EXAMPLE 33

Cholesterol 5α,6α-Epoxide-α,β-Imidazole Dicarboxylic Acid Adduct (Hapten)

Following the procedure of Example 29 cholesterol 5α,6α-epoxide and α,β-imidazole dicarboxylic acid in 1:2 molar ratio under alkaline conditions produce the desired product.

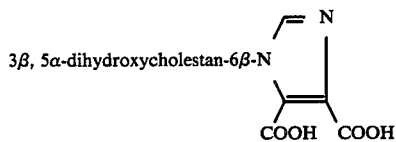

EXAMPLE 34

Cholesterol 5β,6β-Epoxide-α,β-Imidazole Dicarboxylic Acid Adduct (Hapten)

Following the procedure of Example 33 cholesterol 5β,6β-epoxide and α,β-imidazole dicarboxylic acid in 1:2 molar ratio produce the desired product.

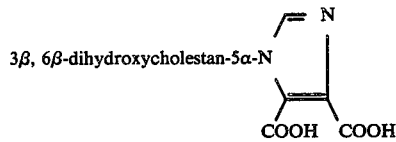

EXAMPLE 35

Cholesterol 5α,6α-Epoxide-Histamine Adduct (Hapten)

Following the procedure of Example 29 the desired product is obtained from cholesterol 5α,6α-epoxide and histamine.

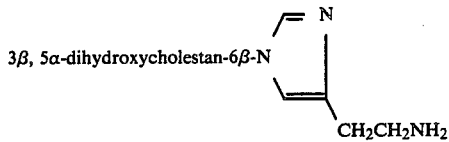

EXAMPLE 36

Cholesterol 5β,6β-Epoxide-Histamine Adduct (Hapten)

Following the procedure of Example 29 the desired product is obtained from cholesterol 5β,6β-epoxide and histamine.

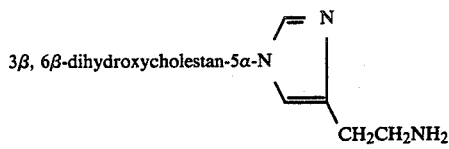

EXAMPLE 37

Cholesterol 5α,6α-Epoxide-Histadine Adduct (Hapten)

Following the procedure of Example 29 the desired product is obtained from cholesterol 5α,6α-epoxide and L-histadine.

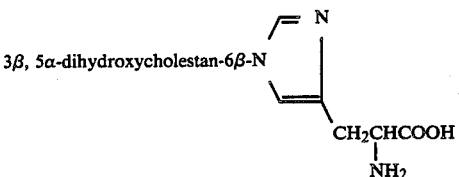

EXAMPLE 38

Cholesterol 5β,6β-Epoxide-Histadine Adduct (Hapten)

Following the procedure of Example 29 the desired product is obtained from cholesterol 5β,6β-epoxide and L-histadine.

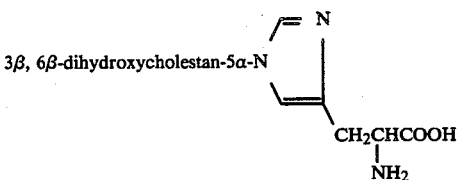

EXAMPLE 39

Cholesterol 5α,6α-Epoxide-Piperidine Adduct
(Hapten)

Following the procedure of Example 29 in either aqueous or aqueous-alcoholic solution the interaction of cholesterol 5α,6α-epoxide and piperidine results in the desired product.

3β, 5α-dihydroxycholestan-6β-N 

EXAMPLE 40

Cholesterol 5β,6β-Epoxide-Piperidine Adduct
(Hapten)

Procedure of Example 29 in aqueous or aqueous-alcoholic solution provides:

3β, 6β-dihydroxycholestan-5α-N 

EXAMPLE 41

Cholesterol 5α,6α-Epoxide-Alkyl Piperidine Adduct
(Hapten)

Procedure of Example 29 in aqueous or aqueous-alcoholic solution provides:

3β, 5α-dihydroxycholestan-6β-N 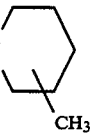

EXAMPLE 42

Cholesterol 5β,6β-Epoxide-Alkyl Piperidine Adduct
(Hapten)

Procedure of Example 29 in aqueous or aqueous-alcohol solution provides:

3β, 6β-dihydroxycholestan-5α-N 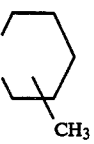

EXAMPLE 43

Cholesterol 5α,6α-Epoxide-Pipecolic Acid Adduct
(Hapten)

Following the procedure of Example 29 in alkaline aqueous or aqueous-alcoholic solution.

3β, 5α-dihydroxycholestan-6β-N 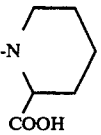

EXAMPLE 44

Cholesterol 5β,6β-Epoxide-Pipecolic Acid Adduct
(Hapten)

Following the procedure of Example 29 in alkaline aqueous or aqueous-alcoholic solution.

3β, 6β-dihydroxycholestan-5α-N 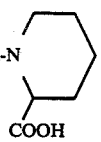

EXAMPLE 45

Cholesterol 5α,6α-Epoxide-Pyrrolidine Adduct
(Hapten)

Following the procedure of Example 29 in aqueous or aqueous-alcoholic solution.

3β, 5α-dihydroxycholestan-6β-N 

EXAMPLE 46

Cholesterol 5β,6β-Epoxide-Pyrrolidine Adduct
(Hapten)

Following the procedure of Example 29 in aqueous or aqueous-alcoholic solution.

3β, 6β-dihydroxycholestan-5α-N 

EXAMPLE 47

Cholesterol 5α,6α-Epoxide-3-Pyrroline Adduct
(Hapten)

Following the procedure of Example 29 in aqueous or aqueous-alcoholic solution.

3β, 5α-dihydroxycholestan-6β-N 

EXAMPLE 48

Cholesterol 5β,6β-Epoxide-3-Pyrroline Adduct
(Hapten)

Following the procedure of Example 29 in aqueous or aqueous-alcoholic solution.

3β, 6β-dihydroxycholestan-5α-N 

EXAMPLE 49

Cholesterol 5α,6α-Epoxide-Amino Acid Adducts (Hapten)

Following the procedure of Example 29 in aqueous or aqueous-alcoholic solution with neutral-alkaline conditions a variety of amino acids can serve as nucleophiles.

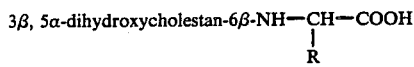

3β, 5α-dihydroxycholestan-6β-NH—CH—COOH
                                   |
                                   R

EXAMPLE 50

With Cholesterol 5β,6β-Epoxide and Amino Acids

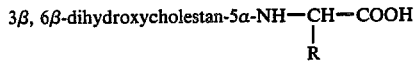

3β, 6β-dihydroxycholestan-5α-NH—CH—COOH
                                   |
                                   R

EXAMPLE 51

6β-N-Propxy-3β,5α-Dihydroxycholestane (Hapten)

In a flask (50 ml) fitted with a condenser cholesterol 5α,6α-epoxide (100 mg., 0.25 mmol) in 1-propanol (20 ml) solution containing trifluoroacetic acid (1.0 ml) is refluxed for 1 hour. With vacuum evaporation the solvent is removed. The oily residue is dissolved in benzene (10 ml), extracted with 5% aqueous sodium bicarbonate (2 ml×2) and with water, and dried with anhydrous sodium sulfate. After vacuum evaporation the amorphous solid residue is purified by silica gel G-60 column liquid chromatography employing chloroform-methanol gradient elution. Selected fractions provide the product, 6β-n-propoxy-3β,5α-dihydroxycholestane. (45 mg).

EXAMPLE 52

5α-N-Butoxy-3β,6β-Dihydroxycholestane (Hapten)

Following the procedure outlined in Example 51, cholesterol 5β,6β-epoxide and 1-butanol with trifluoroacetic acid catalysis provides the product, 5α-m-butoxy-3β,6β-dihydroxycholestane.

Other bulky alkyl alcohols can also be employed for interaction with the cholesterol epoxides to provide alkoxy haptens. Alkoxy groups bulkier than —OCH$_3$ would provide greater specificity with minimum to no cross-reactivity.

EXAMPLE 53

3β,5α-Dihydroxycholestan-6β-N$^6$-Adenine (Hapten)

In a flask (50 ml) fitted with a stirrer cholesterol 5α,6α-epoxide (100 mg., 0.25 mmol.) and adenine (135 mg., 1.0 mmol) dissolved in 50% aqueous ethanol (25 ml) are mixed at 37° for 24 hours. Upon evaporation under vacuum, the resultant reaction residue is extracted with benzene (10 ml.×3). The combined benzene extract is washed with 1% aqueous ammonia and water, and dried with anhydrous sodium sulfate. After vacuum evaporation, the residue is purified by silica gel G-60 liquid chromatography with chloroform-methanol gradient elution. Selected fractions containing the N$^6$-adenine adduct are combined and evaporated under vacuum to yield an amorphous solid (11 mg) as the product.

EXAMPLE 54

3β,6β-Dihydroxycholestan-5α-N$^6$-Adenine (Hapten)

Following the procedure of Example 53, cholesterol 5β,6β-epoxide and adenine react to form the desired adduct product.

EXAMPLE 55

3β,5α-Dihydroxycholestan-6β-N$^2$-Guanine (Hapten)

Following the procedure of Example 53, cholesterol 5α,6α-epoxide and guanine react to form the desired adduct product involving the N$^2$ position of guanine.

EXAMPLE 56

3β,6β-Dihydroxycholestan-5α-N$^2$-Guanine (Hapten)

Following the procedure of Example 53, cholesterol 5β,6β-epoxide and guanine react to form the desired adduct product involving the N$^2$ position of guanine.

The interaction of various purines and pyrimidines and their respective nucleoside and nucleotide derivatives with cholesterol 5α,6α-epoxide and cholesterol 5β,6β-epoxide take place in aqueous or aqueous-alcohol solutions at neutrality producing, respectively, the 3β,5α-dihydroxycholesten-6β- and the 3β,6β-dihydroxycholestan-5α-adduct products. All of the positions of interaction on the purine and pyrimidine molecules are not fully known since mixtures most often result.

The different purines and position of interaction:
N$^6$—adenine (some N$^9$ substitution)
N$^6$—adenosine
N$^6$—3'-adenylic acid
N$^6$—5'-adenylic acid
N$^6$—adenosine diphosphate
N$^6$—adenosine triphosphate
N$^6$—2-methyladenine (some N$^9$ substitution)
N$^2$—guanine (some N$^9$ substitution)
N$^2$-guanosine (some N$^7$ substitution)
N$^2$—3'-guanylic acid (some N$^7$ substitution)
N$^2$—5'-guanylic acid (some N$^7$ substitution)
N$^2$—1-methylguanine (some N$^9$ substitution)

Cholesterol Epoxide Bridge Compounds

EXAMPLE 57

5α,6α-Epoxycholestan-3β-O-Hemisuccinate

In a 500 ml. flask provided with a condenser cholesterol 5α,6α-epoxide (10 gm., 25 mmol) is refluxed with succinic anhydride (5 gm., 50 mmol) in pyridine (100 ml) solution under nitrogen for 12 hours. After cooling benzene (300 ml) and crushed ice are added to the reaction mixture. The cooled solution is slightly acidified with cold aqueous hydrochloric acid with vigorous stirring. Thereafter the cold mixture is extracted with chloroform (100 ml×3). The combined chloroform extracts are washed with water and dried with anhydrous sodium sulfate. Evaporation under vacuum of the chloroform produced an amorphous residue which was triturated with ethyl ether. The hemisuccinate product (6.2 gm) was dried after washing with ice-cold ether.

EXAMPLE 58

5β,6β-Epoxycholestan-3β-O-Hemisuccinate

Following the procedure of Example 57, cholesterol 5β,6β-epoxide (10 gm., 25 mmol) and succinic anhydride (5 gm., 50 mmol) interact to form the desired product (5.5 gm).

EXAMPLE 59

5α,6α-Epoxycholestan-3β-O-Carboxymethyl Ether

In a 500 ml. flask provided with a condenser cholesterol 5α,6α-epoxide (10 gm., 25 mmol) is refluxed with methyl bromoacetate (7 gm., 50 mmol) in pyridine (100 ml) solution under nitrogen for 8 hours. After cooling crushed ice is added to the reaction mixture and chloroform (300 ml) is then added. The chloroform layer is extracted with water washes and then evaporated under vacuum to produce an oily residue. Alcoholic potassium hydroxide (1%, 100 ml) is added to the reaction residue for saponification at 60° in a water bath for 1 hour. Addition of chloroform (100 ml) followed by aqueous washes and drying with anhydrous sodium sulfate produces upon vacuum evaporation an amorphous product (4.0 gm).

EXAMPLE 60

5β,6β-Epoxycholestan-3β-O-Carboxymethyl Ether

Following the procedure of Example 59, cholesterol 5β,6β-epoxide (10 gm., 25 mmol) and methyl bromoacetate (7 gm., 50 mmol) interact and form the desired product (4.8 gm.) after saponification.

EXAMPLE 61

5α-Hydroxycholestan-6β-S-yl-Thiophenol-3β-O-Hemisuccinate

Following the procedure of Example 9, 5α,6α-epoxycholestan-3β-O-hemisuccinate is treated with thiophenol in 1:2 molar ratio in benzene solution containing a trace of concentrated phosphoric acid as catalyst to yield the desired product.

EXAMPLE 62

6β-Hydroxycholestan-5α-S-yl-Thiophenol-3β-O-Carboxymethyl Ether

Following the procedure of Example 9, 5β,6β-epoxycholestan-3β-O-carboxymethyl ether is treated with thiophenol in 1:2 molar ratio in benzene solution containing a trace of concentrated phosphoric acid as catalyst to yield the desired product.

EXAMPLE 63

5α-Hydroxycholestan-6β-O-p-Toluenesulfonate-3β-O-Carboxymethyl Ether

Following the procedure of Example 25, 5α,6α-epoxycholestan-3β-O-carboxymethyl ether is treated with p-toluene sulfonic acid in 1:2 molar ratio in benzene solution to yield the desired product.

EXAMPLE 64

6β-Hydroxycholestan-5α-O-p-Toluenesulfonate-3β-O-Hemisuccinate

Following the procedure of Example 25, 5β,6β-epoxycholestan-3β-O-hemisuccinate is treated with p-toluenesulfonic acid in 1:2 molar ratio in benzene solution to yield the desired product.

EXAMPLE 65

5α-Hydroxycholestan-6β-N-yl-Imidazole-3β-O-Carboxymethyl Ether

Following the procedure of Example 29, 5α,6α-epoxycholestan-3β-O-carboxymethyl ether is treated with imidazole in 1:2 molar ratio in ethanol at alkaline reaction to yield the desired product.

EXAMPLE 66

6β-Hydroxycholestan-5α-O-Ethoxy-3β-O-Hemisuccinate

Following the procedure of Example 51, 5β,6β-epoxycholestan-3-β-O-hemisuccinate in ethanol solution is treated with trifluoroacetic acid to yield the desired product.

EXAMPLE 67

Bovine Serum Albumin-5α,6α-Epoxycholestan-3β-O-Hemisuccinate Coupling (Immunogen)

A mixture of purified 5α,6α-epoxycholestan-3β-O-hemisuccinate (100 mg) in dioxane (10 ml), 1-ethyl-3-(3-dimethylaminopropyl)-carbodiimide hydrochloride (100 mg) in water (5 ml) and crystalline bovine serum albumin (BSA, 200 mg) in 0.05N phosphate buffer, pH 7.8 (10 ml) is stirred at room temperature for 24 hours. The reaction mixture is then dialyzed against water for 48 hours at 5° in the refrigerator. The non-permeable material retained after dialysis is then centrifuged at $12000 \times g$ (20 min), and the supernatant is lyophilized, yielding a light product residue (160 mg). The product reveals no free hapten and contains on the average 9 residues of hapten to each BSA molecule. When necessary the steroid-protein complexes are also purified to remove free hapten by G-25 sephadex gel filtration.

EXAMPLE 68

Bovine Serum Albumin-5β,6β-Epoxycholestan-3β-O-Hemisuccinate Coupling (Immunogen)

Following the procedure of Example 67, 5β,6β-epoxycholestan-3β-O-hemisuccinate is coupled to bovine serum albumin, and the resultant steroid-protein complex is isolated and purified.

EXAMPLE 69

Bovine Serium Albumin-5α-6α-Epoxycholestan-3β-O-Carboxymethyl Ether Coupling (Immunogen)

Following the procedure of Example 67, 5α,6α-epoxycholestan-3β-O-carboxymethyl ether is coupled to bovine serum albumin, and the resultant steroid-protein complex is isolated and purified.

EXAMPLE 70

Bovine Serum Albumin-5β,6β-Epoxycholestan-3β-O-Carboxymethyl Ether Coupling (Immunogen)

Following the procedure of Example 67, 5β,6β-epoxycholestan-3β-O-carboxymethyl ether is coupled to bovine serum albumin, and the resultant steroid-protein complex is isolated and purified.

EXAMPLE 71

Bovine Serum
Albumin-6β-Hydroxycholestan-5α-O-Ethoxy-3β-O-
Hemisuccinate Coupling (Immunogen)

Following the procedure of Example 67, 6β-hydroxycholestan-5α-O-ethoxy-3β-O-hemisuccinate is coupled to bovine serum albumin, and the resultant steroid-protein complex is isolated and purified.

EXAMPLE 72

Bovine Serum
Albumin-5α-Hydroxycholestan-6β-S-yl-Thiophenol-
3β-O-Hemisuccinate Coupling (Immunogen)

Following the procedure of Example 67, 5α-hydroxycholestan-6β-S-yl-thiopenol-3β-O-hemisuccinate is coupled to bovine serum albumin, and the resultant steroid-protein complex is isolated and purified.

EXAMPLE 73

Bovine Serum
Albumin-5α-Hydroxycholestan-6β-N-yl-Imidazole-3β-
O-Carboxymethyl Ether Coupling (Immunogen)

Following the procedure of Example 67, 5α-hydroxycholestan-6β-N-yl-imidazole-3β-O-carboxymethyl ether is coupled to bovine serum albumin, and the resultant steroid-protein complex is isolated and purified.

EXAMPLE 74

Bovine Serum
Albumin-5α-Hydroxycholestan-6β-S-yl-Glutathione-
3β-O-Carboxymethyl Ether Coupled Adduct
(Immunogen)

A mixture of purified 5α, 6α-epoxycholestan-3β-O-carboxymethyl ether (100 mg) in dioxane (10 ml), 1-ethyl-3-(3-dimethylaminopropyl)-carbodiimide hydrochloride (100 mg) in water (5 ml) and crystalline bovine serum albumin (200 mg) in 0.05N phosphate buffer, pH 7.8 (10 ml) is stirred at room temperature for 24 hours. The reaction mixture is then dialyzed against water for 48 hours at 5° in the refrigerator. The non-permeable fraction is then centrifuged at 12000×g for 20 minutes. The supernatant is then treated with glutathione (300 mg) for 72 hours at 5° in the refrigerator. In an alternating procedure the supernatant is treated with glutathione in the presence of rat liver S-glutathione transferase B. According to the procedure of Example 5A, after reaction the product is purified by dialysis and G-25 sephadex gel filtration.

EXAMPLE 75 Cl Bovine Serum
Albumin-6β-Hydroxycholestan-5α-S-yl-Glutathione-
3β-O-Hemisuccinate Couple Adduct (Immunogen)

Following the procedures of Example 74, bovine serum albumin is coupled to 5β,6β-epoxycholestan-3β-O-hemisuccinate and then interacted with gluthathione either chemically or enzymatically to produce the product adduct immunogen.

Immunological Procedures

Immunization—Antigen (steroid-BSA conjugate, 5 to 15 mg per animal) is dissolved in 2 ml saline and emulsified with an equal volume of complete Freund's adjuvant (CFA). This emulsion is injected once into multiple intradermal and subcutaneous sites along both sides of the back of 4-monthold male rabbits. The rabbits are bled weekly from the marginal ear vein, starting two weeks after the injection. Goats (mature females, intact or ovariectomized) receive 4 subcutaneous injections of 3 mg antigen emulsified in CFA at weekly intervals, followed by booster injections at 6 to 7 week intervals. Blood samples are drawn from the jugular vein 5 weeks after the first injection and two weeks after each booster injection. Undiluted sera are stored at 4° C. for up to 9 months.

Radioimmunoassay—Sera are diluted with 0.05M Tris-HCl buffer (pH 8.0) containing 0.1M NaCl and 0.1% $NaN_3$ to the extent required, so that 40–45% of a fixed amount of the homologous tritiated steroid (12–18 pg) bound to antibody, as indicated by a preliminary titration. To 0.4 ml lots of the diluted serum placed in 10×75 mm disposable test tubes, varying amounts $(0.5 \times 10^{-11}$ to $10^{-8}$ g) of unlabeled hapten or of heterologous steroids are added in 0.1 ml of the same buffer (10 μg/ml ethanolic solutions of the cold steroids are diluted with buffer to the required concentration). This mixture is incubated for 30 minutes at 0° C. before adding a fixed amount (12–18 pg) of the homologous tritiated steroid in 0.1 ml Tris buffer, and then kept for another 3 h at 0° C. (This "pre-emptive" method of adding the cold steroid or unknown sample to the antiserum before the labeled steroid in our hands slightly enhances the sensitivity of the assay, compared to the "equilibrium" technique of adding the two steroid species simultaneously). The remaining free steriod is then removed by adding 0.1 ml of a suspension of dextran-coated charcoal in Tris buffer (0.5% w/v Norit A activated charcoal and 0.5% w/v Dextran T20), stirring for 10 minutes at 0° C. and centrifugation at 2200×g for 20 mnutes at 4° C. A portion (0.5 ml) of the supernatant is withdrawn into a counting vial containing Insta-Gel (Packard Instrument Co.) for determination of the bound radioactive steroid by liquid scintillation counting.

Immunization Procedure

A great variety of immunization procedures may be employed for the production of antisera to steroids. Common practice is to inject only adjuvants emulsions subcutaneously or intramuscularly, footpad injection (either subcutaneous or intradermal) and the intranodal route, although the latter method is complicated by the technical difficulty of locating and injecting a number of separate lymph nodes at open operation.

A preferred method is the multiple intradermal injection procedure in which the immunogen emulsion is injected at 40 or more sites spread over a considerable part of the body surface. Antibody response is relatively rapid and booster injections have little further effect.

While almost all routes of administration such as subcutaneous, intramuscular, intravenous, into the lymph nodes or footpads are applied in connection with subsequent booster injections, only the multiple-site intradermal immunization appears to yield satisfactory results without booster injections.

A great variety of animal species may be used for immunization, including rabbits, sheep, goats, and guinea pigs.

The preferred embodiments described above are not intended to be limiting. Variations in the materials and processes described will be apparent to those skilled in the art. Thus, the present invention is to be limited only by the scope of the appended claims.

What is claimed is:

1. A method for determining the presence or concentration of 5α,6α- and 5β,6β-cholesterol epoxide in a fluid containing said epoxides comprising:

contacting said fluid with a hapten in the presence of a hapten-linking reagent to convert said epoxides to ring-opened 3,5(6)-trans-diaxial-dihydroxycholestane-6(5)yl-hapten adduct;

combining said adduct with a measured amount of said adduct, said measured amount of adduct being labelled with a colorimetrically, spectrophotometrically or radioactively measurable label;

combining said adduct and measured adduct with an excess of an antibody to said adduct;

and measuring the amount of labelled adduct bound to said antibody.

2. The method according to claim 1 wherein said labelled adduct is labelled with a substance which is spectrophotometrically measurable.

3. A method for determining the presence of a concentration of 5α,6α and 5β,6β cholesterol epoxide in a fluid containing said epoxides, comprising:

contacting said fluid with a hapten in the presence of a hapten-linking reagent to convert said epoxides to ring-opened trans-3,5(6)-trans-diaxial-dihydroxycholestane-6(5)-yl-hapten adduct;

combining said adduct with an excess of a measured amount of a labelled antibody to said adduct;

separating unbound labelled antibody from bound labelled antibody;

measuring the amount of labelled antibody bound to said adduct.

4. The method according to claim 3 wherein said antibody is labelled with a substance which is colorimetrically measurable.

5. The method according to claim 1 or 3 wherein said labelled antibody or labelled adduct is labelled with a radioactive isotope.

6. The method according to claim 1 or 3 wherein said hapten is comprised essentially of glutathione and said hapten-linking reagent comprises S-glutathione transferase.

7. An immunogen comprising a 3,5(6)-trans-diaxial-dihydroxy-cholestane-6(5)-yl-hapten adduct.

8. An immunogen according to claim 7 wherein said adduct is linked through covalently bonded bridges to a protein.

9. An immunogen according to claim 7 or 8 wherein said hapten comprises glutathione.

* * * * *